United States Patent [19]

Bharadwaj et al.

[11] Patent Number: 5,639,929
[45] Date of Patent: Jun. 17, 1997

[54] OXIDATIVE DEHYDROGENATION PROCESS

[75] Inventors: Sameer S. Bharadwaj; Lanny D. Schmidt, both of Minneapolis, Minn.

[73] Assignee: Regents of the University of Minnesota, Minneapolis, Minn.

[21] Appl. No.: 422,787

[22] Filed: Apr. 17, 1995

[51] Int. Cl.$^6$ .................. C07C 5/327; C07C 5/333
[52] U.S. Cl. .................. 585/658; 585/654; 585/656; 585/659; 585/660; 585/661
[58] Field of Search .................. 585/654, 656, 585/658, 659, 660, 661

[56] References Cited

U.S. PATENT DOCUMENTS

| | | | |
|---|---|---|---|
| 4,529,374 | 7/1985 | Malik et al. | 431/7 |
| 4,758,375 | 7/1988 | Brophy et al. | 252/373 |
| 4,767,569 | 8/1988 | Brophy et al. | 252/373 |
| 4,940,826 | 7/1990 | Font Freide et al. | 585/600 |
| 5,105,052 | 4/1992 | Font Freide et al. | 585/651 |
| 5,186,859 | 2/1993 | Sie | 252/373 |
| 5,382,741 | 1/1995 | Astbury et al. | 585/652 |

FOREIGN PATENT DOCUMENTS

| | | |
|---|---|---|
| 0164864 | 12/1985 | European Pat. Off. . |
| 0178853 | 4/1986 | European Pat. Off. . |
| 0332289 | 9/1989 | European Pat. Off. . |
| 0561439 | 9/1993 | European Pat. Off. . |
| 0576096 | 12/1993 | European Pat. Off. . |

OTHER PUBLICATIONS

Xiang, Sheng, Song, Guifen & Lin. New Method For Olefin Production From Light Alkanes. React. Kingt. Catal. Lett., vol. 53, pp. 205–209, 1994.

*Primary Examiner*—Glenn A. Caldarola
*Assistant Examiner*—Elizabeth D. Wood
*Attorney, Agent, or Firm*—Kenneth H. Johnson

[57] ABSTRACT

A process for the oxidative dehydrogenation of hydrocarbons is disclosed in which $C_2$–$C_6$ alkanes are contacted with an oxygen containing gas in a fluidized catalyst bed of platinum, rhodium, nickel or platinum-gold supported on $\alpha$-alumina or zirconia. Ethane is dehydrogenated to ethylene and higher alkanes are dehydrogenated to ethylene, propylene and iso-butylene.

20 Claims, 5 Drawing Sheets

OXIDATIVE DEHYDROGENATION PROCESS

This invention was made with government support under Grant No. CTS-9311295 awarded by the NSF. The government has certain rights in the invention.

BACKGROUND OF THE INVENTION

1. Field of the Invention

The present invention relates to a fluidized bed process for the oxidative dehydrogenation of organic compounds to produce olefins utilizing a fluidized bed of supported platinum, rhodium or nickel particles.

2. Related Art

The abundant supplies of light alkanes (methane, ethane, propane, normal butane and iso-butane) have led to greater utilization of them as feedstocks rather than fuel. The light alkanes are the preferred feed stocks for producing olefins by thermal pyrolysis. However, thermal dehydrogenation processes for olefin production are highly endothermic and require complex tube furnaces. In addition excess steam (about 50% by volume) is necessary to slow coke formation, and the products contain acetylenes, diolefins and aromatics in addition to the desired olefins.

Early U.S. Pat. Nos. 3,420,911; 3,420,912; 3,440,299 and 3,428,703 disclose a moving bed solid oxidant used for oxidative dehydrogenation of organic compounds. The oxidant, a metal ferrite in a moving bed is contacted with the organic compound in the presence of oxygen and steam in a reaction zone to remove hydrogen producing compounds of higher unsaturation. The oxygen deficient bed moves to a reoxidation zone and hence back to the rezone and so forth.

Okagami et al in U.S. Pat. No. 3,541,179 suggest utilizing copper, manganese, chromium, vanadium, zinc, silver or cadmium supported on a refractory material and in a fluidized mode for oxidative dehydrogenation of hydrocarbons. Brophy, et al in U.S. Pat. No. 4,767,569 suggest an oxidative dehydrogenation process utilizing an inert particulate catalyst in a spouting bed mode wherein the hydrocarbon and oxygen stream are fed at a flow rate sufficient to produce a spouting action of the bed material whereby at least a part of the particulate catalyst is thrown up above the bed surface and subsequently falls back into the bed.

Freide, et al in U.S. Pat. No. 4,940,826 suggest utilizing a particulate catalyst having a platinum group metal supported thereon in lieu of the inert material of Brophy to produce olefins when feeding ethane and higher alkanes.

SUMMARY OF THE INVENTION

Briefly the present invention is a process for the oxidative dehydrogenation of organic compounds by contacting the organic compounds with a fluidized bed comprising catalyst selected from the group consisting of platinum, rhodium, nickel and platinum-gold on a particulate support in the presence of oxygen containing gas, preferably at mole ratios of organic compound to oxygen in the range of 1.4:1 to 2.2:1 and preferably for contact times from 0.05 to 0.50 seconds and more preferably residence time of the combined streams is between 50 and 200 milliseconds. Preferably paraffin hydrocarbons are used as the feed, such as $C_2$ to $C_6$ alkane.

In a preferred embodiment olefins are produced from the catalytic oxidative dehydrogenation of ethane, propane, and butanes utilizing α-alumina or zirconia beads coated with Pt in a fluidized bed reactor.

DESCRIPTION OF THE PREFERRED EMBODIMENT

In olefin production utilizing platinum supported catalyst the selectivity of ethane to ethylene was observed to be above 70% with conversions above 85% at the oxidative dehydrogenation stoichiometry (alkane/$O_2$=2.0). Using rhodium supported catalyst at the oxidative dehydrogenation stoichiometry selectivities to olefins up to 60% at about 75% ethane conversion were obtained.

Propane and butane over the platinum supported catalyst produced olefin selectivities of 55–60% and 65–70% respectively with greater than 90% conversion for both alkanes. Ethylene production dominated at higher temperatures and longer contact times while propylene production was favored at lower temperatures and shorter contact times. When iso-butane was used over the platinum catalyst the olefin selectivity was observed to be 60–70% with about 80% conversion with iso-butylene and propylene the predominant olefins. For all alkanes acetylene formation was less than 0.8% and the combined diolefin ($C_4H_6$) and aromatic production was less than 0.05%.

Although all of the experiments were carried out in a regime which predicted severe coke forming, no carbon buildup was observed on any of the catalyst and no evidence of deactivation was observed over several days.

The reactions for normal-butane are listed below as an example.

A. Exothermic Reactions:

In the presence of $O_2$ hydrocarbons can be totally or partially oxidized depending on the feed composition (hydrocarbon/$O_2$). In increasing order of the hydrocarbon/$O_2$ ratio they can either be totally oxidized (1), partially oxidized to syngas (2) or oxidatively dehydrogenated to the corresponding olefin (3). Butane can also be oxidatively cracked (4).

$C_4H_{10}+13/2O_2 \rightarrow 4CO_2+5H_2O$ combustion (1)

$C_4H_{10}+2O_2 \rightarrow 4CO+5H_2O$ syngas (2)

$$C_4H_{10}+1/2O_2 \rightarrow C_4H_8+H_2O \text{ olefins} \quad (3)$$

$$C_4H_{10}+1/2O_2 \rightarrow 2C_2H_4+H_2O \text{ cracking} \quad (4)$$

B. Endothermic Reactions:

Besides oxidation reactions, dehydrogenation (5) and cracking (6,7) reactions can also take place at high temperatures.

$$C_4H_{10} \rightarrow C_4H_8+H_2 \text{ dehydrogenation} \quad (5)$$

$$C_4H_{10} \rightarrow CH_4+C_3H_6 \text{ cracking} \quad (6)$$

$$C_4H_{10} \rightarrow C_2H_4+C_2H_6 \text{ cracking} \quad (7)$$

C. Carbon Forming Reactions:

The product species can also react to form solid carbon ($C_s$) via olefin cracking (8), CO disproportionation (Boudouard reaction) (9), and reverse steam reforming of carbon (10).

$$\text{olefin} \rightarrow C_s+H_2 \text{ olefin cracking} \quad (8)$$

$$2CO \rightarrow C_s+CO_2 \text{ CO disproportionation} \quad (9)$$

$$CO+H_2 \rightarrow C_s+H_2O \text{ reverse steam reforming} \quad (10)$$

Published thermodynamic equilibrium calculations predict solid graphite to be the major product at all temperatures for hydrocarbon/$O_2$ compositions richer than that for syngas, and at lower temperatures graphite is stable at even leaner hydrocarbon compositions. Evaluation of "experimental equilibrium constants" suggested that on platinum the olefin cracking reaction (8) did not reach equilibrium and the $CO_2$ and $H_2O$ partial pressures were high enough to suppress graphite formation caused by alkane and olefin cracking by $CO_2$ and steam reforming of $C_s$—equations (9) and (10).

Calculations of the "experimental equilibrium constants" (ratios of partial pressures given by equilibrium equations) for reactions (8) to (10) show that on Pt and Rh olefin cracking reactions do not reach equilibrium and that the $CO_2$ and $H_2O$ partial pressures are high enough to suppress graphite formation by CO disproportionation and reverse steam reforming. On Pd, equilibrium in all reactions leads to heavy carbon buildup. Ni is intermediate between Pt and Pd because some carbon formation on the reactor walls during operation was observed. However, the rates were very slow and the catalyst did not deactivate over a period of 4 hours.

With iso-butane, adsorption of the tertiary carbon atom followed by β-hydrogen elimination leads to iso-butylene. Adsorption of a primary carbon leads to $C_3H_6$ and $CH_4$ via elimination of a β-methyl. CO, $CO_2$, $CH_4$ and $H_2O$ are produced either by α-methyl elimination from a tertiary butyl or α-hydrogen elimination from a primary iso-butyl.

Iso-butylene is chiefly used to produce methyl tertiarybutyl ether (MTBE). In current commercial processes, thermal dehydrogenation of iso-butane gives iso-butylene yields up to 20%. However, the process is highly endothermic and byproducts such as diolefins and aromatics are also obtained. Although good selectivities to isobutylene (≈80%) have been achieved with catalytic oxidative dehydrogenation on a number of oxide catalysts, the low conversions (<10%) make the yields unacceptable.

Carbon formation takes place either by olefin cracking, CO disproportionation or reverse steam reforming of carbon as shown before in reactions (8) to (10). Continued formation of even traces of solid carbon on the catalyst will completely shut the reaction off very quickly. No evidence of carbon buildup on Pt or Rh at steady state was observed in the present experiments. This of course does not imply that there is no carbon on the catalyst but that a true steady state is attained where carbon is gasified at exactly the same rate at which it is deposited. In fact, sometimes at very rich feed compositions (fuel/$O_2$>2.1) it was observed that the few catalyst particles that accumulated in the expansion zone were black. However, when these were shaken back into the reactor they were regenerated so no black particles were seen in the gray Pt catalyst at the end of the experiment or any deactivation over a period of >10 hours of operation.

The supports may be any low surface area refractory material such as alumina, zirconia, quartz, carborundum, or ceramic of a particle size to be fluidized by the reaction stream gases, generally 0.01 to 10 mm. Low surface area materials are those having surface areas less than 1 $m^2$/gm, preferably the particle size is 1–150 μm.

EXAMPLES

All of the examples were carried out in a 3.2 cm diameter quartz tube reactor having an expanded section at the top for catalyst disengagement using 15–20 gm of catalyst. The unfluidized bed depth was about 2 cm and the expansion was approximately a factor of two which corresponded to a solid fraction about 0.25. Depending on total flow rate and bed expansion the contact times at reaction temperature (about 850° C.) and nearly complete conversion were between 0.05 and 0.5 seconds. A porous 40μ quartz frit served as a gas distributor and support plate. The entire reactor was wound with high temperature heating tape and insulated. Gas flow into the reactor was controlled by mass flow controllers, preferably below that which would cause a spouting action within said bed. The feed flow rates ranged from 0.5 to 2.0 standard liters per minute total flow, corresponding to 1.0 to 4.0 cm/s superficial velocity (i.e. the velocity of the feed gases upstream from the catalyst) at room temperature and atmospheric pressure. The product gases were sampled just before the expansion with a gas tight syringe through a septum covered sample port or through heated lines leading to the gas chromatograph (GC). A coarse 175μ pyrex frit was loosely fitted in the disengagement section to prevent blowout of fines.

The GC analysis was performed using a single Hayesep DB packed column with temperature programming. For quantitative determination of concentrations, standards were used for all species except $H_2O$ which was obtained most reliably from an oxygen atom balance. The mole number change due to reaction was determined by an atomic balance on nitrogen, and 15–25% $N_2$ was added for oxygen experiments. The product gas carbon atom and hydrogen balances typically closed to within ±2%.

Temperatures were monitored using two thermocouples, one before the quartz frit and one in the catalyst bed. In order to determine the heat input through the heating tape, the feed gas temperature and bed temperature were measured for a fixed power input without reaction by flowing air through the reactor.

The catalysts were prepared by deposition and decomposition of the respective salts on low surface area, attrition resistant α-$Al_2O_3$ supports (with the exception of the platinum zirconia catalyst). The alumina spheres, specially prepared for fluidization applications, were supplied by Norton Chemical Process Products Corporation and had a particle size range of 80–100 μm, surface area of about 0.3 $m^2$/gm and internal pore volume of about 0.2 $cm^3$/gm. The bulk density of the fixed bed was about 1.1 gm/$cm^3$. For metal deposition, the alumina was stirred in a heated salt solution of known concentration until most of the water evaporated.

The wet spheres were dried and then calcined for 2–3 hours at the appropriate temperature to decompose the salt. Catalysts with loadings of 0.25–2.0% by weight were prepared.

Light-off was achieved by preheating the catalyst bed to 300°–350° C. in air or $N_2$ and then introducing the hydrocarbon/$O_2$ mixture. At light-off the temperature rose rapidly and attained steady state (700°–800° C.) within a few minutes which was a function of the overall heat generation rate due to chemical reaction, the heat input through the heating tape, the energy carried by the products gases and the rate of energy loss from the reactor by conduction, convection and radiation.

Throughout these experiments no changes in activity or selectivities were detected from 10 minutes after ignition to at least 5 hours of operation for fixed inlet conditions. Identical steady state temperatures and product compositions could be repeated on returning to the original conditions after several changes in feed conditions and flow rates. Positioning of the thermocouple at different locations in the catalyst bed indicated that the bed was isothermal within ±2% and no hot spots were detected which indicated good solids mixing in the fluidized bed.

In the examples the effects of feed composition, reaction temperatures and flow rates were examined for all the $C_1$–$C_4$ alkanes on platinum catalysts. Experiments were performed using both air and almost pure $O_2$ (15% $N_2$ diluent). All results are shown below as selectivities calculated on a carbon or hydrogen atom basis.

Several different catalysts were examined with ethane. Platinum was found to be the best catalyst for ethylene, Pt—Au gave very similar results, while Rh and Ni produced $C_2H_4$ with selectivities up to 60% near the oxidative dehydrogenation stoichiometry. On Pd, reactions eventually go to chemical equilibrium which produces carbon. Pt/$ZrO_2$ gives slightly better conversions and lower selectivities than Pt/$Al_2O_3$.

Example 1

Ethane

In FIGS. 1a–1d are shown the fractional carbon and hydrogen atom selectivities, conversions and temperatures for feed mixtures of ethane and air on Pt and Rh as a function of the feed composition. Identical conditions (flow, heat input and composition) in the same reactor allowed observations for Pt and Rh to be compared directly. The feed composition was varied maintaining constant total flow rate (1.5 slpm) and heat input. To facilitate comparison with $O_2$ experiments shown later, the feed composition is represented by the $C_2H_6/O_2$ ratio rather than % ethane in air. The $C_2H_6/O_2$ ratio for syngas is 1.0 and that for oxidative dehydrogenation is 2.0. Experiments were performed in the range of 0.8 to 2.2 and the $O_2$ conversion was complete at all compositions.

As seen in FIGS. 1a–1d, at $C_2H_6/O_2$=0.8, the CO and $H_2$ selectivities on Rh are ≈90% with complete ethane conversion and no ethylene formation. However, on Pt at the same composition, the CO and $H_2$ selectivities are lower (≈35%) while ethylene is produced with 37% selectivity with 96% ethane conversion. This is surprising since, as noted above, thermodynamics predicts CO, $H_2$, $CH_4$ and graphite with no other significant byproducts. As the $C_2H_6/O_2$ ratio is increased, the ethylene selectivity increases on both metals. At the oxidative dehydrogenation stoichiometry (2.0), the ethylene selectivity on Pt reaches as high as 70% while that on Rh reaches 60%. The conversion on both is ≈75% which corresponds to ethylene yields of 52.5% on Pt and 45% on Rh. Beyond $C_2H_6/O_2$=2, there is no significant gain in selectivity and the conversion drops.

Figure 1A:
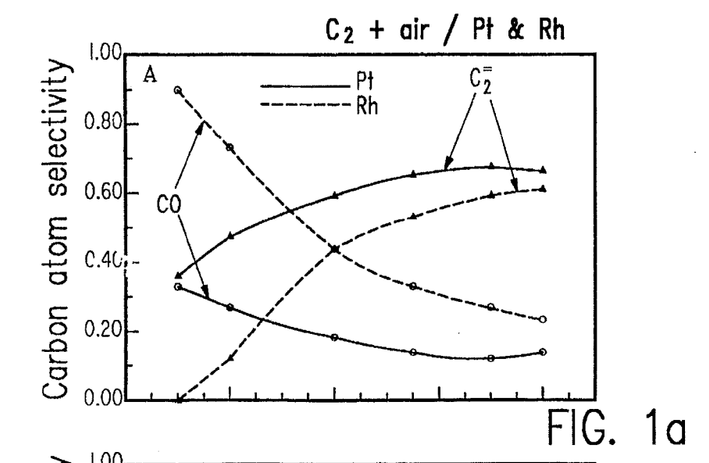
FIGS. 1a–1d shows the fractional carbon and hydrogen atom selectivities, conversions and temperatures for feed mixtures of ethane and air on Pt and Rh as a function of the feed composition.
Figure 1B:
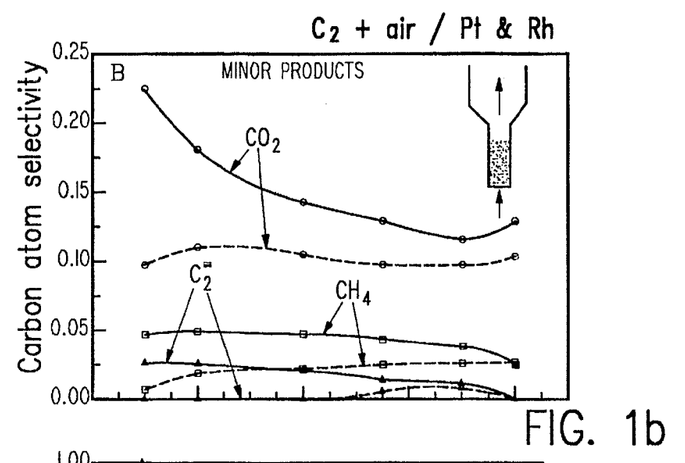
Figure 1C:
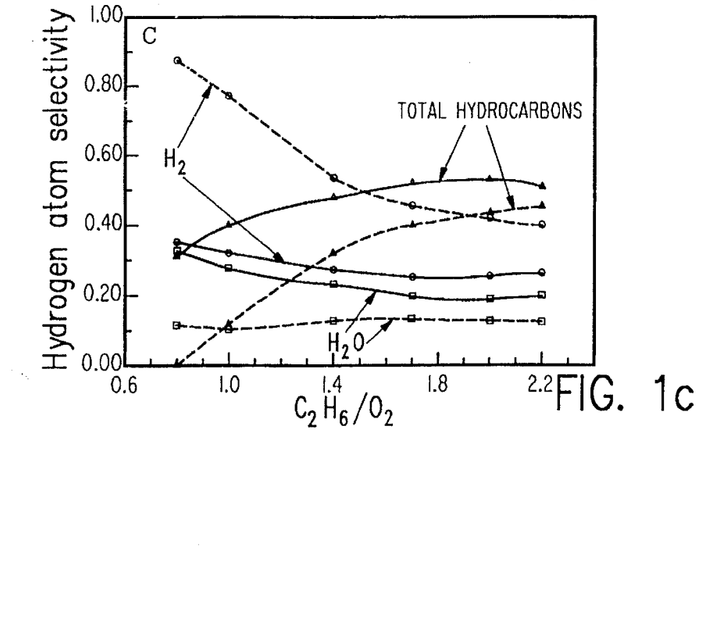
Figure 1D:
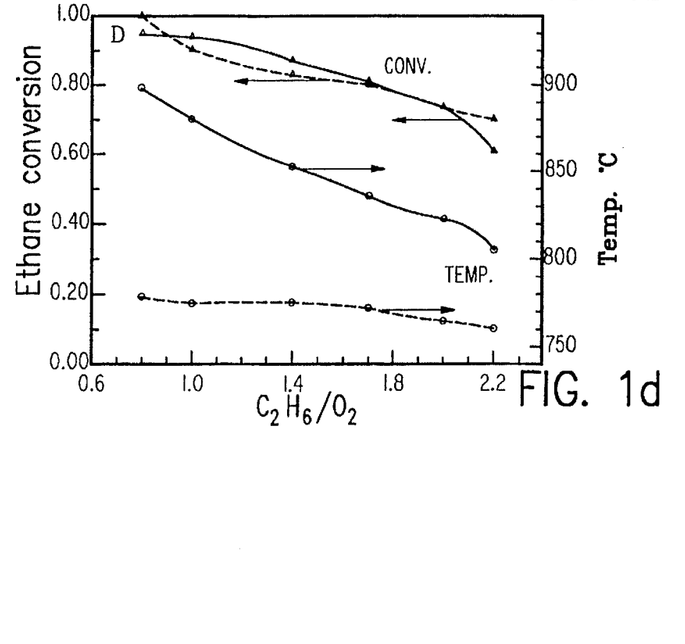
Figure 2A:
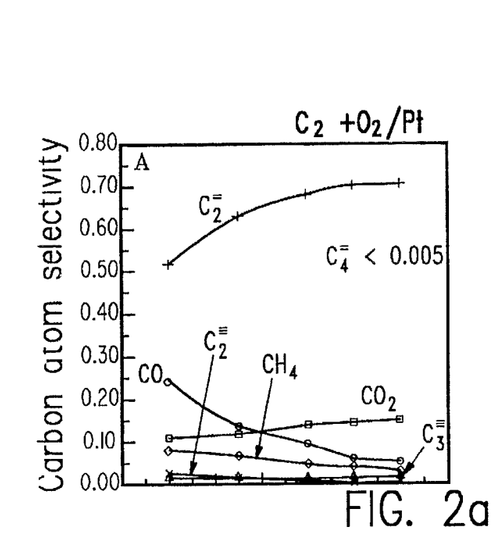
FIGS. 2a and 2b, the carbon selectivities, conversion and bed temperature for ethane oxidation in $O_2$ on Pt are shown as a function of feed composition.
Figure 2B:
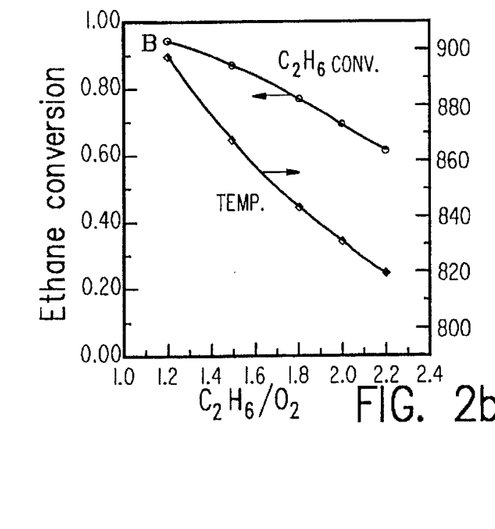

In FIGS. 2a and 2b, the carbon selectivities, conversion and bed temperature for ethane oxidation in $O_2$ on Pt are shown as a function of feed composition. The feed composition was varied maintaining 15% $N_2$ in the feed at a total flow rate of 1.5 slpm. The observed trends were similar to those for the air experiments. In the presence of reduced $N_2$ diluent, the reaction temperatures were higher. At $C_2H_6/O_2$=2, the ethylene selectivity and ethane conversion were 72% and 70% respectively giving a yield of 50.4%.

Figure 2C:
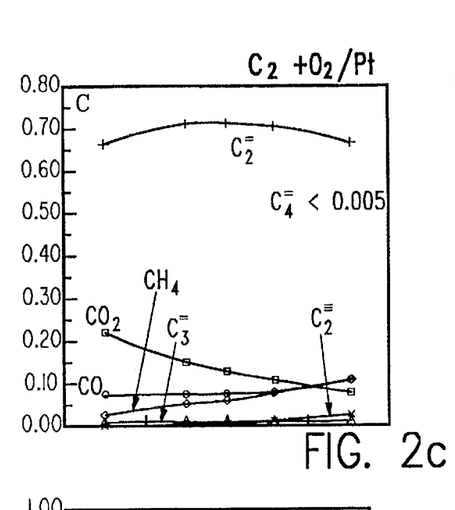
FIGS. 2c and 2d show the conversion is improved by increasing the reaction temperature.
Figure 2D:
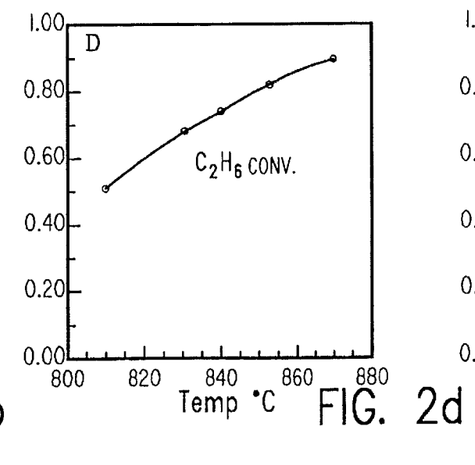

The conversion can be improved by increasing the reaction temperature as shown in FIGS. 2c and 2d. The reaction temperature Was varied by varying the heat input at fixed flow rate (1.5 slpm) and composition ($C_2H_6/O_2$=2). With an increase in temperature to 870° C., ethane conversion exceeds 90% and ethylene selectivity drops to 67%. However, yields in excess of 60% are obtained (86% conversion with 70% selectivity or 90% conversion with 67% selectivity) which are considerably higher than those obtained in thermal pyrolysis in a single pass.

Figure 2E:
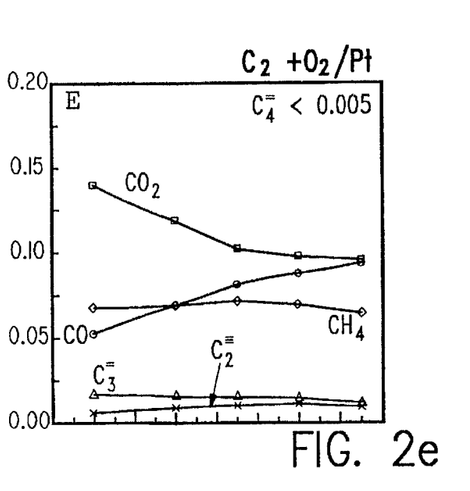
FIGS. 2e and 2f illustrate the effect of flow rate on the selectivities, conversions and temperatures at $C_2H_6/O_2=2$ for fixed heat input.
Figure 2F:
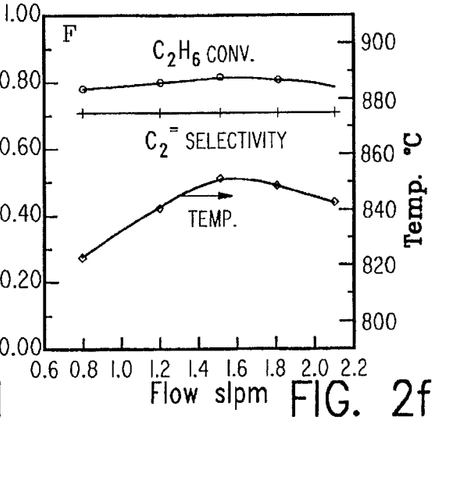

FIGS. 2e and 2f illustrate the effect of flow rate on the selectivities, conversions and temperatures at $C_2H_6/O_2$=2 for fixed heat input. It can be seen that a threefold variation in superficial contact time produces no significant change in the ethylene selectivity (≈70%) and ethane conversion (80%).

Figure 3A:
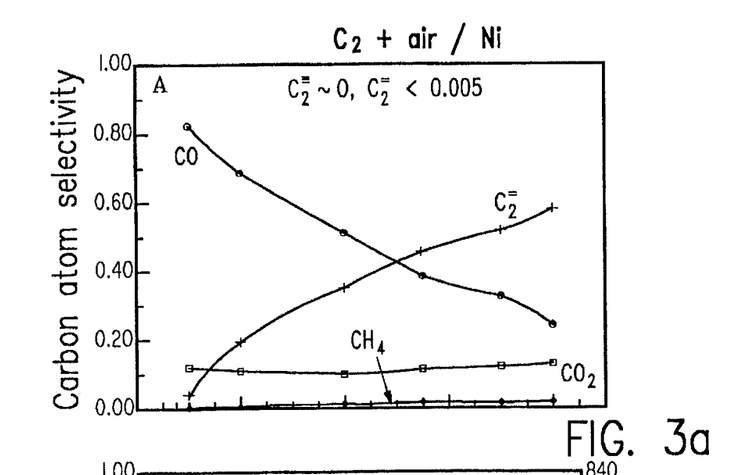
FIGS. 3a and 3b show the effect of ethane feed composition on carbon selectivities, conversion and temperature for ethane oxidation on Ni in air.
Figure 3B:
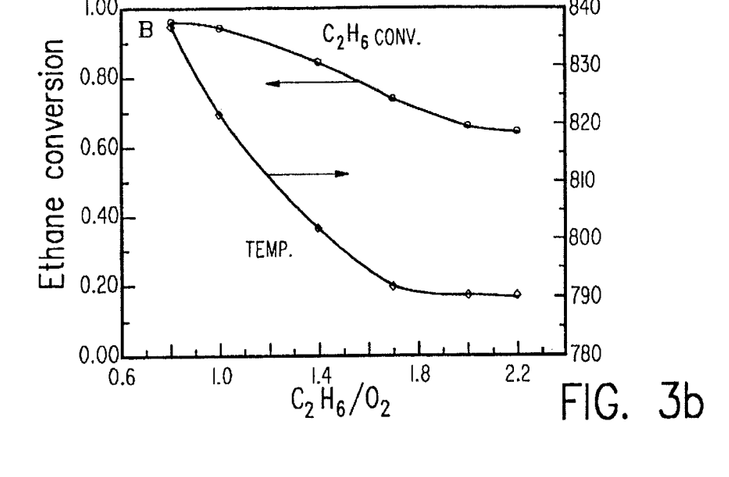

Ni and Pd catalysts on the same $\alpha$-$Al_2O_3$ support were also examined. FIGS. 3a and 3b show the effect of ethane feed composition on carbon selectivities, conversion and temperature for ethane oxidation on Ni in air. Nickel is seen to be very similar to Rh with high CO and $H_2$ selectivities near the syngas stoichiometry and ethylene selectivity up to 60% at the oxidative dehydrogenation stoichiometry. With Pd, the catalyst rapidly coked after light-off and the reaction shut off in less than 10 minutes.

Platinum-gold catalyst was also examined with the aim of reducing the hydrogenolysis activity by reducing Pt ensemble size by Au addition. However, results obtained with Pt—Au were very similar to those for Pt suggesting that the hydrogenolysis activity was low. With Pt/$ZrO_2$, slightly higher conversions and lower selectivities to ethylene were observed than with Pt/$Al_2O_3$.

Figure 3C:
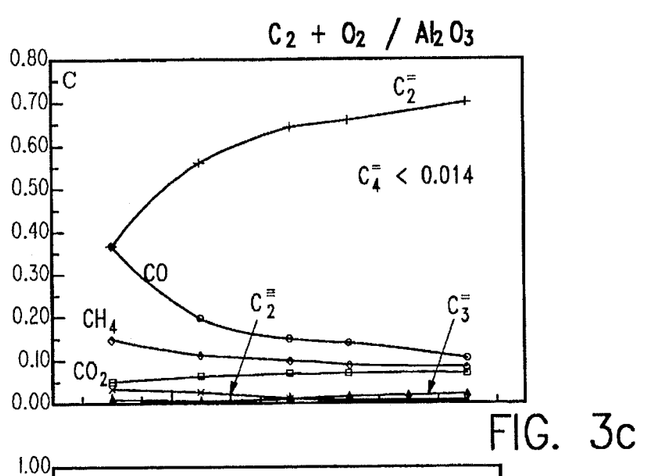
FIGS. 3c and 3d show the selectivities, conversions and temperatures for ethane oxidation with $O_2$ on $Al_2O_3$ as a function of the feed composition.
Figure 3D:
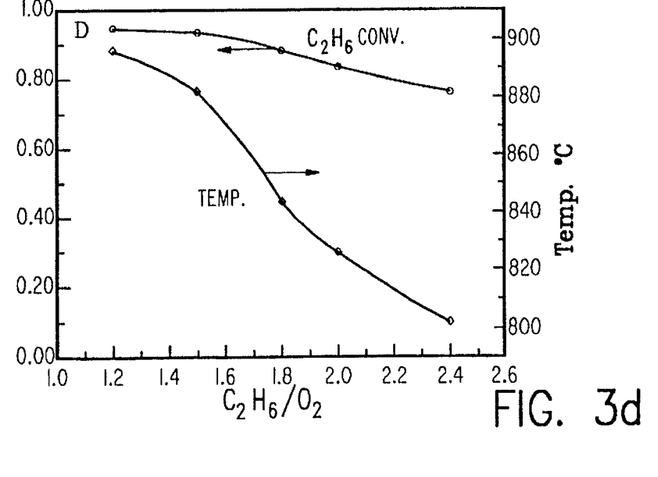

Experiments were also performed with pure $Al_2O_3$ to study the activity of the support. With $Al_2O_3$, unlike Pt and Rh, light-off is very difficult and gradual and a much higher heat input is required to achieve high temperatures for acceptable yields. FIGS. 3c and 3d show the selectivities, conversions and temperatures for ethane oxidation with $O_2$ on $Al_2O_3$ as a function of the feed composition. More CO versus $CO_2$ is obtained on $Al_2O_3$ than on Pt, which explains the need for higher heat input because $CO_2$ formation is much more exothermic. Also $CH_4$ production is significantly greater on $Al_2O_3$ and is >10% compared to <5% on Pt. At $C_2H_6/O_2$=2, the ethylene selectivity and ethane conversion on $Al_2O_3$ are 67% and 83% respectively. Optimum yields are obtained at temperatures near ≈810° C. Beyond $C_2H_6/O_2$=2, although the ethylene selectivity continues to increase, higher heat input is necessary to sustain high temperatures for high conversion. At $C_2H_6/O_2$=3, the ethylene selectivity is 82% and the conversion is 72% (with higher heat input). $\alpha$-$Al_2O_3$ did not coke even at fuel/$O_2$ ratios>3.5. Also, the particles that accumulated in the expansion zone were clean and white.

Example 2

Propane and N-butane on pt

Propane and n-butane oxidation on 0.5 wt. % Pt/$Al_2O_3$ were examined using both air and $O_2$. Since the results with air and $O_2$ were quite similar (the only difference being higher temperatures obtained with $O_2$), only the $O_2$ data are shown. Ethylene and propylene were the major olefins obtained from both alkanes and the product distributions had similar features suggesting that the mechanism for olefin formation was the same for both hydrocarbons. In FIGS. 4a–4f, are shown selectivity and conversion data for n-butane. Data for propane are not shown because trends for propane can be deduced from n-butane data.

Figure 4A:
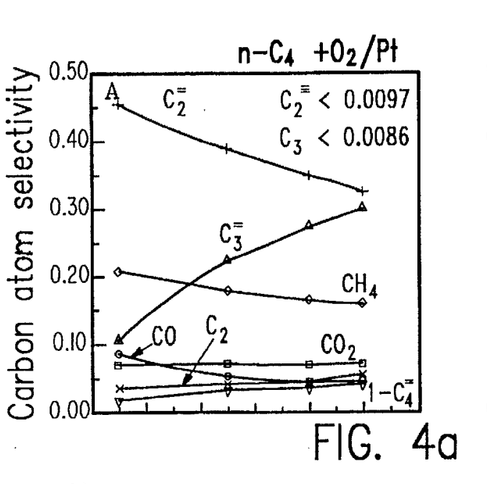
FIGS. 4a–4f show selectivity and conversion data for n-butane.
Figure 4B:
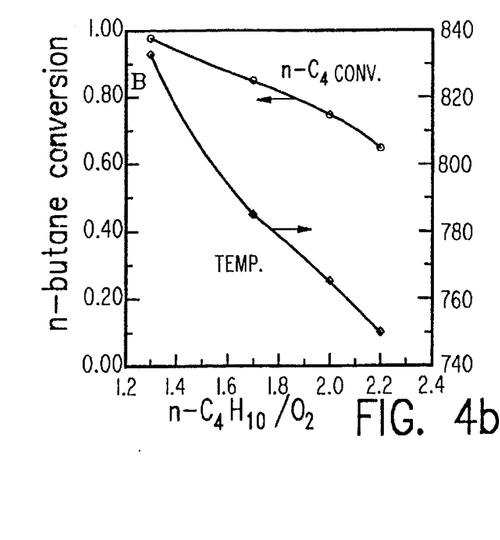

In FIGS. 4a and 4b, are shown the selectivities, conversion and temperature for n-butane oxidation with $O_2$ on Pt as a function of the feed n-$C_4H_{10}/O_2$ ratio. At low feed composition (n-$C_4H_{10}/O_2$=1.3), butane conversion is nearly complete with a total olefin selectivity of ≈59% ($C_2^=:C_3^=:C_4^==46:11:2$). As the feed composition is increased, the temperatures and conversions decreased with the total olefin selectivity rising to 66% ($C_2^=:C_3^=:1-C_4^==36:27:3$) at the oxidative dehydrogenation stoichiometry (n-$C_4H_{10}/O_2$=2.0). An increase in feed composition causes the ethylene selectivity to decrease while the propylene selectivity increases. Also the ratio of the $C_2H_4$ and $CH_4$ carbon atom selectivities is ≈2 over the entire composition range suggesting that the process involves cracking of propylene into $C_2H_4$ and $CH_4$.

Figure 4C:
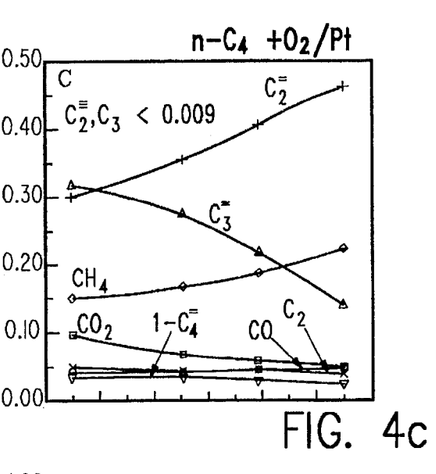
Figure 4D:
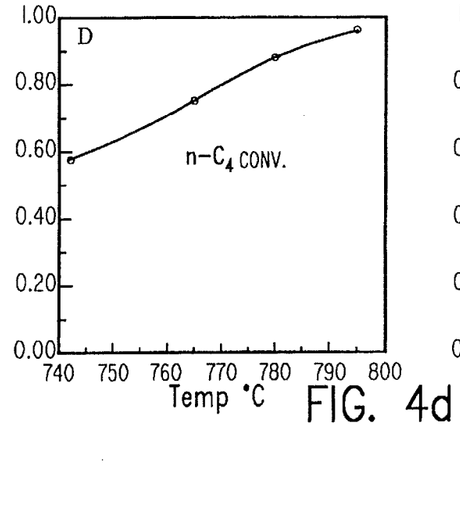

The effect of temperature on the selectivities and conversions at n-$C_4H_{10}/O_2$=2.0 is shown in FIGS. 4c and 4d. It can be seen that by increasing the temperature the conversion which is 60% at 745° C. can be increased to almost 95% at ≈800° C. The total olefin selectivity drops slightly from 65% to 61%. An opposite trend in the olefin selectivity distribution may be noted. With increasing temperature, more ethylene and $CH_4$ and less propylene were produced.

Figure 4E:
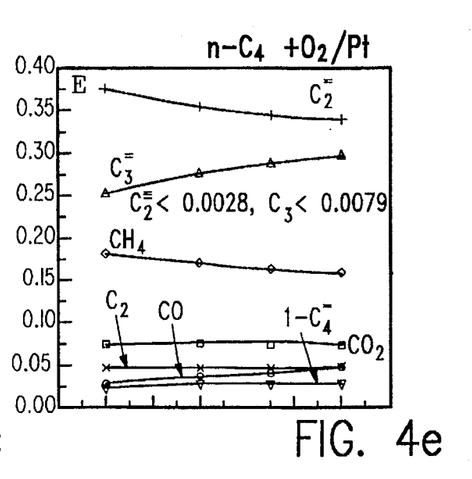
Figure 4F:
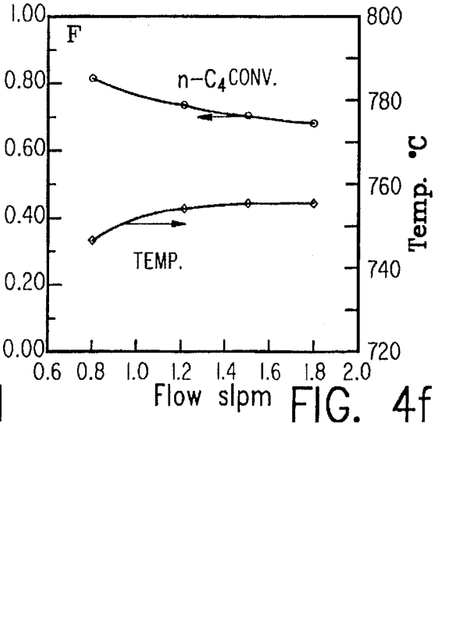

FIGS. 4e and 4f show the effects of varying the contact time at n-$C_4H_{10}/O_2$=2.0 for fixed heat input. With increasing flow rate, there was a slight increase in the total olefin selectivity along with a small drop in conversion. As expected, propylene increased while ethylene and $CH_4$ both decreased in the same manner as before. The survival of propylene with decreasing contact time strongly suggests that the mechanism involves cracking of propylene.

Results with propane were very similar. In summary, both propane and n-butane can be converted to olefins with 60–70% selectivity and 90%+ conversion. Ethylene production dominates at high temperatures and long contact times while propylene production is maximized at lower temperatures and short contact times. Very low amounts of butenes are produced with n-butane which cracks readily to give lower olefins.

Example 3

Iso-butane on Pt

Figure 5A:
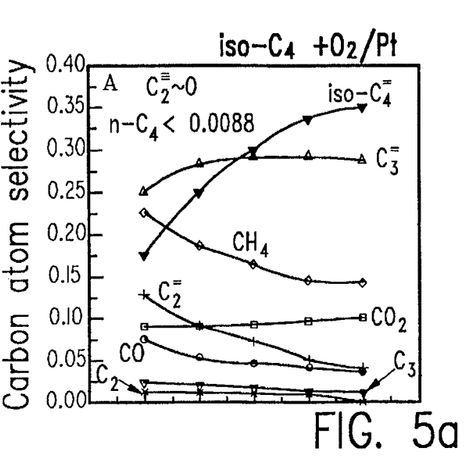
FIGS. 5a and 5b are shown the selectivities, conversion and temperature for iso-butane oxidation with $O_2$ on Pt as a function of the feed composition at fixed flow rate and heat input.
Figure 5B:
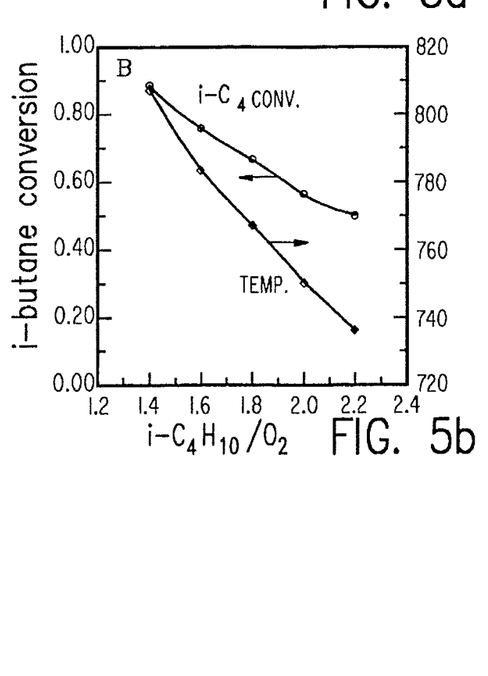

In the fluidized bed experiments iso-butane conversions in excess of 80% can be achieved with total olefin selectivities between 60–70%. In FIGS. 5a and 5b are shown the selectivities, conversion and temperature for iso-butane oxidation with $O_2$ on Pt as a function of the feed composition at fixed flow rate and heat input. At i-$C_4H_{10}/O_2$=1.4, the conversion was 90% and the total olefin selectivity was 55% (i-$C_4^=:C_3^=:C_2^==17.5:25:12.5$). As the feed composition is increased to i-$C_4H_{10}/O_2$=2.0, the total olefin selectivity increased to 68% (i$C_4^=$: $C_3^=$: $C_2^==34:29.5:5.1$) while the conversion dropped to 56%. The olefin distributions show that as the composition approached that for oxidative dehydrogenation, iso-butylene and propylene selectivities increased while the ethylene and $CH_4$ selectivities decreased.

Figure 5C:
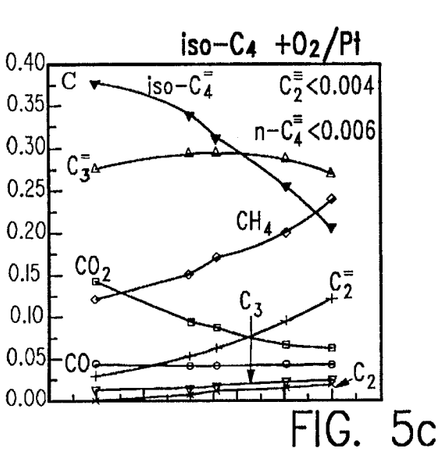
FIGS. 5c and 5d show the effect of temperature on the selectivities and conversions at $i\text{-}C_4H_{10}/O_2=2.0$.
Figure 5D:
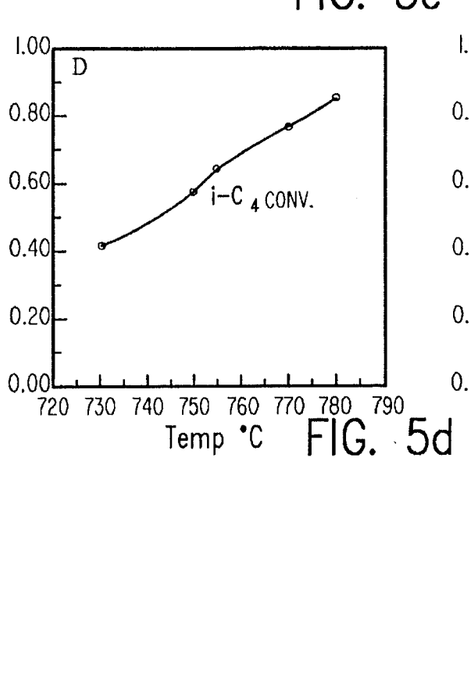

FIGS. 5c and 5d show the effect of temperature on the selectivities and conversions at i-$C_4H_{10}/O_2$=2.0. Increase in temperature from 730 to 780° C. was accompanied by a decrease in total olefin selectivity from 69 to 60% while the conversion increased from 42 to 86%. Also with increasing temperature more ethylene and $CH_4$ and less isobutylene were produced. The propylene selectivity did not vary much with temperature.

Figure 5E:
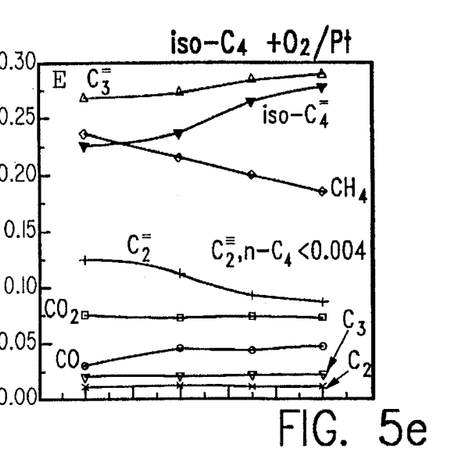
FIGS. 5e and 5f show the results of flow rate variation at $i\text{-}C_4H_{10}/O_2=2.0$ for a fixed heat input.
Figure 5F:
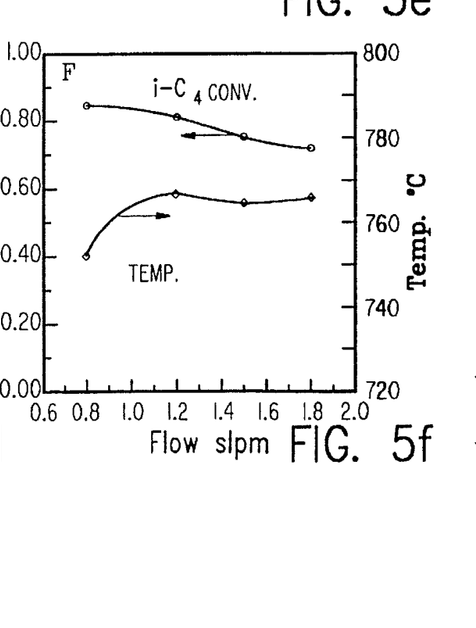

In FIGS. 5a–d it can be seen that iso-butylene production was maximized at high alkane compositions (near i-$C_4H_{10}/O_2$=2.0) and lower temperatures. However, at low temperatures, conversions were lower (>60%). To increase conversion the temperature needed to be increased which decreased iso-butylene selectivity. This decrease might be prevented if the contact time were reduced. In FIGS. 5e and 5f, are shown the results of flow rate variation at i-$C_4H_{10}/O_2$=2.0 for a fixed heat input. As expected, with increasing flow rates an increase in iso-butylene and propylene selectivities was observed with a decrease in ethylene and $CH_4$. The conversion drops slightly.

The autothermal temperatures (no external heating) were typically between 550–850° C. for room temperature feed gases, depending on the stoichiometric composition of the hydrocarbon/$O_2$ mixture, $N_2$ diluent, amount of catalyst in the reactor, flow rate, and the reactor used. With richer feeds, less exothermal reactions take place, giving lower autothermal temperatures. Moreover, in a fluidized bed the high heat transfer coefficients and solids backmixing promote heat losses. In most experiments the reactor was heated externally to raise the temperature of the reaction mixture above 750° C. to achieve better yields. The problem of heat losses is typical in small scale equipment. A large scale reactor, on the other hand, is expected to operate at higher autothermal temperatures eliminating the need for additional heat input.

The fluidized bed was well mixed with respect to the catalyst. The solids backmixing efficiently carried heat back upstream to maintain isothermal conditions throughout the reactor.

In the fluidized bed the gases were probably close to plug flow. It is believed that almost all the $O_2$ is consumed close to the distributor region. Flow past the small 100 μm particles at high velocities (22.5 cm/s at reaction conditions) results in thin boundary layers and enhanced mass transfer rates which result in rapid and complete $O_2$ consumption. If the region containing $O_2$ is assumed to be 2 mm thick, the contact time at reaction conditions is 8.9 milliseconds. Therefore, once all the $O_2$ has been reacted, the olefins leave the reactor without reacting further. Higher gas backmixing would lead to olefin +$O_2$ reactions and selectivity loss because olefins are more reactive than alkanes, and at lower flow rates selectivity losses were seen.

The invention claimed is:

1. A process for the oxidative dehydrogenation of organic compounds comprising contacting saturated organic compounds under oxidative dehydrogenation conditions with a fluidized bed comprising catalyst selected from the group consisting of platinum, rhodium, nickel and platinum-gold on a particulate support in the presence of oxygen containing gas to produce organic compounds having at least one double bond.

2. The process according to claim 1 wherein the mole ratio of organic compounds to oxygen in the range of 1.4:1 to 2.2:1.

3. The process according to claim 1 wherein said organic compounds comprise paraffin hydrocarbons.

4. The process according to claim 3 wherein said paraffin hydrocarbons comprise $C_2$ to $C_6$ alkane.

5. The process according to claim 4 wherein said alkane comprises ethane.

6. The process according to claim 4 wherein said alkane comprises propane.

7. The process according to claim 4 wherein said alkane comprises n-butane.

8. The process according to claim 4 wherein said alkane comprises isobutane.

9. The process according to claim 1 wherein said support comprises α-alumina coated with platinum.

10. The process according to claim 1 wherein said support comprises zirconia coated with platinum.

11. The process according to claim 1 wherein said contacting is for periods of from 0.05 to 0.50 seconds.

12. A process for the oxidative dehydrogenation of hydrocarbons comprising feeding a saturated hydrocarbon stream and an oxygen containing gas stream under oxidative dehydrogenation conditions to a reactor containing a catalyst bed of platinum, rhodium, nickel or platinum-gold supported particulate catalyst, the flow rate of the combined streams being sufficient to fluidize said bed to produce hydrocarbons having at least one double bond.

13. The process according to claim 12 wherein the flow rate is below that which would cause a spouting action within said bed.

14. The process according to claim 12 wherein said hydrocarbon stream contains ethane, propane or butane and the respective products are ethylene, propylene or butene.

15. The process according to claim 12 wherein the temperature within said bed is between 550° C. and 850° C. and the residence time of the combined streams is between 50 and 200 milliseconds.

16. The process according to claim 12 wherein said hydrocarbon stream contains ethane and said catalyst bed comprises platinum and the product comprises ethylene.

17. The process according to claim 12 wherein said hydrocarbon stream contains propane and said catalyst bed comprises platinum and the products comprise ethylene and propylene.

18. The process according to claim 12 wherein said hydrocarbon stream contains normal butane and said catalyst bed comprises platinum and the products comprise ethylene and propylene.

19. The process according to claim 12 wherein said hydrocarbon stream contains iso-butane and said catalyst bed comprises platinum and the products comprise isobutylene and propylene.

20. The process according to claim 12 wherein said support comprises α-alumina particles having a particle size of between 80 and 100 μm, a surface of about 0.3 $m^2/gm$ and internal pore volume of about 0.2 $cm^3/gm$.

* * * * *